United States Patent [19]

Narita et al.

[11] 4,170,139

[45] Oct. 9, 1979

[54] SAMPLING DEVICE FOR ANALYSIS OF MOLTEN METAL FOR HYDROGEN

[75] Inventors: Kiichi Narita; Hiroshi Hara, both of Kobe; Masayuki Taniguchi, Ono; Masaru Yamaguchi, Akashi; Iwao Matumoto, Kobe, all of Japan

[73] Assignee: Kobe Steel, Ltd., Kobe, Japan

[21] Appl. No.: 902,450

[22] Filed: May 3, 1978

[30] Foreign Application Priority Data

May 6, 1977 [JP] Japan ............................ 52-57788[U]
Dec. 21, 1977 [JP] Japan ............................ 52-173109[U]

[51] Int. Cl.$^2$ .................................................. G01N 1/14
[52] U.S. Cl. ......................................................... 73/425.6
[58] Field of Search ............... 73/DIG. 9, 19, 425.4, 73/425.6

[56] References Cited

U.S. PATENT DOCUMENTS

| | | | |
|---|---|---|---|
| 3,369,406 | 2/1968 | Lowdermilk | 73/425.6 |
| 3,886,444 | 5/1975 | Roy et al. | 73/19 |
| 3,967,505 | 7/1976 | Feichtinger | 73/DIG. 9 |

*Primary Examiner*—S. Clement Swisher
*Attorney, Agent, or Firm*—Oblon, Fisher, Spivak, McClelland & Maier

[57] ABSTRACT

A sampling device for a quantitative determination of hydrogen in molten metal, which includes a material in which hydrogen is relatively non-diffusible during testing or readily soluble during sampling and a refractory vessel housing this material. This refractory vessel is sealed so as to maintain a vacuum or negative (reduced) pressure therein, and is provided with a thin-walled aspirating portion which is readily destroyed by an external pressure.

7 Claims, 9 Drawing Figures

SAMPLING DEVICE FOR ANALYSIS OF MOLTEN METAL FOR HYDROGEN

BACKGROUND OF THE INVENTION

1. Field of the Art

This invention relates to a sampling device for a rapid and accurate determination of hydrogen in molten metal.

2. Description of the Prior Art

The hydrogen contained in a metallic material has a significant influence upon the properties of the metal. By way of example, a high concentration of hydrogen in a steel-making material not only leads to brittleness but can be a cause of serious defects such as white spots and fractures. Therefore, it is of vital importance that the behavior of hydrogen be accurately monitored throughout the melting process, e.g. in molten iron and molten steel, so that the hydrogen content of the material will be controlled within an appropriate range. This requirement will be met only if a procedure is established for an accurate determination of hydrogen in molten metal. To this end, it is essential that a truly representative sample be obtained from the molten metal bath to be analyzed without losses or pick-up of hydrogen. Various samplers have heretofore been proposed to meet the above requirement but none of the devices thus far developed is fully satisfactory.

The prior art sampling techniques applicable to molten metal, particularly to molten steel, may be classified into the following two categories, as now discussed below.

The a first method comprises quenching the sample at a sufficiently rapid rate to "freeze in" in the hydrogen in the molten steel within the sample.

Specifically, (1) a spoon-mould process, (2) an aspiration process (3) an evacuated quartz-tube process, etc. may be mentioned.

These processes excel in workability and, hence, are in widespread use but unless the quenching operation is performed with sufficient efficiency, a loss of hydrogen takes place, which inevidatably precludes a complete trapping of the hydrogen. The result is that these procedures yield fairly lower values than the true value although the magnitude of error depends on the level of hydrogen and the type of alloy.

A second method involves the provision of a reservoir in the sampling device for the hydrogen that is released during the quenching and solidification of the sample within the sampler. Specifically, the vacuum sampling as is explained in papers of 19th committee of "NIPPON GAKUJUTSU SHIKOOKAI", (H. Freichtinger method and other procedures are known and, in theory, ought to give true hydrogen values. By these procedures, however, the gaseous hydrogen and the residual hydrogen in the solidified specimen must be independently determined. This not only means that the workability is low but also implies increased chances of an analytical error. Moreover, the sample must of necessity be of complicated construction and the chance of success in obtaining a sample is low. Thus, apparently these techniques have not been employed commonly in practical operations.

Asise from the above procedures, the technique called the immersion mould or J. G. Bassett method was proposed as disclosed in "The Determination of Gases in Metals, The Iron and Steel Institute (1960)", at page 12. This method involves the use of a device, which, as illustrated in FIG. 1 (A), comprises a quartz tube 1, a copper mould 2 as fitted into the tube 1, a sealing means 3 and a thin-walled portion 5. If necessary, the internal cavity 4 of the mould is evacuated. With this device, the molten metal breaks through the thin-walled portion 5 into the cavity 4 of the mould. Since, by this method, it is no longer necessary to take a sample with a spoon, the loss of hydrogen at the time of sampling is reduced. Moreover, because the mould 2 is made of copper, the quenching effect on molten metal is high. The quenched and solidified metal is a removed from the resultant specimen is analyzed for hydrogen. While the loss of hydrogen at sampling is, therefore, low, the hydrogen released in the process of quenching is not measured. Thus, the method is still not free from the disadvantages that the values are lower then the true hydrogen contents, ant that the quenching effect is not sufficient. In the taking of a sample from a molten metal for analysis, the supersaturating hydrogen is released as the result of the reduced solubility of hydrogen due to a sharp reduction in temperature of the specimen. Therefore, the loss of hydrogen is inevitable in the sampling stage and, in the above-described prior art methods, this loss of hydrogen has to be practically disregarded.

Illustrated in FIG. 1 (B) is a sampler which is most commonly utilized today. The reference numeral 1 indicates a quartz tube having a thin-walled portion 5. A substantial vacuum is maintained within the quartz tube 1 and, when the molten metal is sampled, the portion of the specimen obtained in a central part of the sampler is less porous than the portion of the same specimen obtained in the part other than said central portion.

However, with a sampler of the type illustrated in FIG. 1 (B), it is still difficult to prevent a diffusion of hydrogen up to the time when the final analytical data are obtained and experience has shown that the results are often lower than the expected values.

This invention has been accomplished in view of the above disadvantages of the prior art procedures.

SUMMARY OF THE INVENTION

It is a primary object of this invention to provide a sampling device such that in the determination of hydrogen in a molten metal, the loss of hydrogen from a specimen at the time of sampling may be precluded.

It is another object of this invention to provide a sampling device such that the hydrogen released during the period from the time of sampling to the time of analysis may also be included in the analysis.

For the purpose of accomplishing the above and other objects, this invention provides, in one aspect, a sampling device for an analysis of a molten metal for hydrogen, which comprises a refractory containment member having a thin-walled aspirating portion which is easily destroyable by an external force and a material in which hydrogen is either relatively non-diffusible during testing readily soluble during sampling a vacuum or reduced pressure being maintained within said containment member.

In a second aspect, this invention relates to a sampling device similar to said first embodiment, wherein a tubular member made of a metallic material which is capable of alloying with the molten metal to be sampled is inserted and disposed inside the refractory containment member in such relationship that a clearance is formed between the outer wall of the tubular member and the inner wall of the refractory containment member.

In a third aspect, this invention relates to a sampling device similar to said first embodiment wherein a tubular member of austenite stainless steel is disposed inside a refractory containment member of quartz, a substantial vacuum being maintained in the containment member, and the refractory containment member is provided at its forward end with a thin-walled portion which is easily destroyable by an external force.

In a fourth aspect, this invention is directed to a sampling device similar to the first embodiment wherein said refractory containment member is provided at its forward end with a curved portion.

In a fifth aspect, this invention relates to a sampling device similar to the second embodiment wherein the refractory containment member is provided at its forward end with a curved portion.

In a sixth aspect, this invention relates to a sampling device similar to the second embodiment wherein the containment member of quartz is provided, on its inner wall, with a plurality of projections extending toward the axis thereof and said clearance is defined by and between said containment member and a tubular member of pure titanium.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 (B) is a longitudinal cross-sectional view showing another prior art sampling device for measurement of hydrogen or other component of a molten metal.

DETAILED DESCRIPTION OF THE PREFERRED EMBODIMENTS

Figure 2:
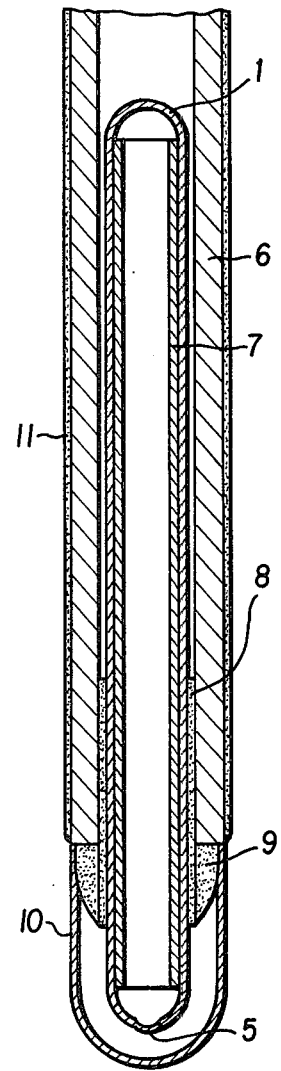
FIG. 2 is a longitudinal cross-sectional view showing an embodiment of the sampling device according to this invention.

Referring now to the drawings, wherein like reference numerals designate identical or corresponding parts throughout the several views, and more particularly to FIG. 2 which illustrates an embodiment of this invention, a refractory tubular containment member 1 of quartz is housed in a protective member 6 of paper (e.g. a paper sleeve) and a thin-walled tubular member 7 whose outer diameter is slightly smaller than the inner diameter of quartz tube 1 is encased in the quarts tube leaving a small clearance between the quartz tube 1 and thin-walled tubular member 7. This clearance is intended to ensure an efficient removal of quartz from the thin-walled tubular member 7 when the quarts tube 1 is quenched and crushed. As the material for the refractory containment member 1, quartz may be replaced with any other suitable refractory material. As the material for the thin-walled tube 7, a material in which hydrogen is relatively non-diffusible during testing or readily soluble during sampling is recommended. This, as typical examples, high Ni-Cr alloy steel, Ti, Zr, Nb, Ta, etc. may be mentioned, although austenite stainless steel is used in the present embodiment. An increased precision of analysis may be achieved by ensuring that the hydrogen content of such metal is lower than about 2 ppm. This is because, with the sampling device of this invention, the thin-walled tube 7 is also a substrate for hydrogen analysis. The size of the thin-walled tube 7 is another factor influencing the accuracy of results and, in consideration of this fact, when a tubular member like that illustrated is employed, it preferably satisfies the following conditions as to the reaction of outer diameter ($R_1$) with inner diameter ($R_2$):

$$R_1^2 - R_2^2 < 1 \tag{1}$$

$$4\text{mm} \leq R_1 \leq 20 \text{ mm} \tag{2}$$

While the overall length of this thin-walled tube may vary somewhat with different applications, it is generally within the range of 100 to 200 mm, preferably about 60 to 120 mm. As to the thin-walled tubular member 7, while a tube 7 open at both ends is shown, the end (the top end as shown) opposite to the aspiration end may of course be closed to present a configuration similar to that of a test tube. The degree of vacuum or reduced pressure within the quartz tube is not a critical limiting factor in this invention but, to ensure a smooth aspiration and filling of molten metal, it is preferable that a pressure of less than 0.3 atmosphere be maintained.

Referring to FIG. 2, a paper sleeve 6 with a surface coating of mortar 11 and the quartz tube 1 are disposed in such relation as to provide a narrow clearance therebetween, thereby facilitating a withdrawal of the quartz tube as being quenched. However, to prevent the sleeve from being slipped off during the sampling operation, asbestos 8 is filled into the clearance and a head 9 of bonding cement is formd at the foward end of paper sleeve 6. Furthermore, a cap 10 made of aluminum is fitted so as to protect the thin-walled portion 5 when the sampler is not used. If the sampler is dipped into molten steel with the aluminum cap 10 on, the cap not only prevents the thin-walled portion 5 from beng contaminated by the slag on the surface of the steel bath but is instrumental in that the time from the time of sipping to the time when the aluminum melts to expose the thin-walled portion 5 and the latter breaks can be somewhat delayed. Thus, the provision of the cap is advantageous in that a sample may be taken in an optional part of the body of molten steel. In this particular case, a Cu cap may be used. The sampling device illustrated in FIG. 2 is formd as a device of the vertical type so that it can be conveniently applied to the taking of a molten steel sample from a converter, ladle, casting mould or the like.

Figure 3:
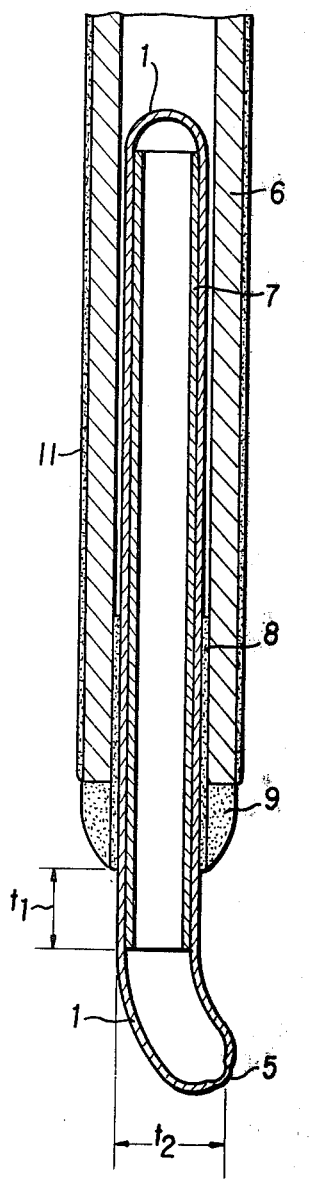
FIG. 3 is a longitudinal cross-sectional view showing another embodiment of the sampling device according to this invention.

For the purpose of taking a specimen from the teeming stream of molten steel in the ingot-making process, it is advantageous to bend the tip of the quartz tube 1 as illustrated in FIG. 3 and collect the sample by dipping the sampler in a horizontal direction with respect to the teeming stream. The sampler shown in FIG. 2 can be immersed deep into the steel bath, then, the thin-walled portion (5) is readily destroyed by the pressure of molten metal. Since the sampling device of FIG. 3 cannot be deeply immersed, its thin-walled portion 5 desirably has a somewhat increased area so that it may be readily broken by the external pressure.

Figure 4:
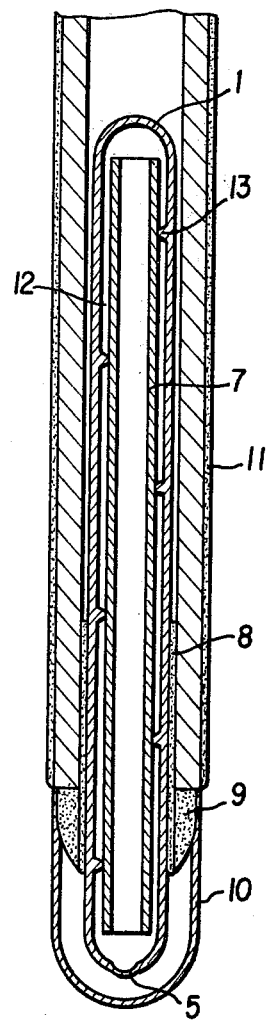
FIG. 4 is a longitudinal cross-sectional view showing still another embodiment of the sampling device according to this invention.
Figure 5:
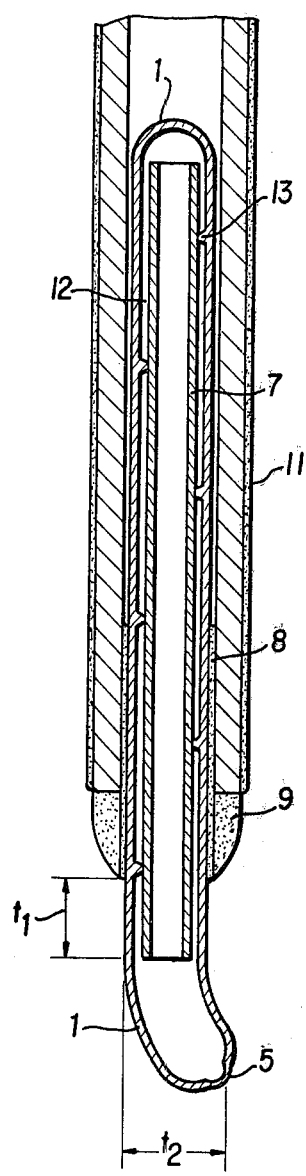
FIG. 5 is a longitudinal cross-sectional view showing yet another embodiment of the sampling device according to this invention.

The sampling device illustrated in FIGS. 4 and 5 further includes a thin-walled tubular member 7 of metal having an outer diameter smaller than the inner diameter of quartz tube 1, for example by about 2 mm. Defined by the outer wall of the metallic tubular member 7 and the inner wall of said quartz tube 1 is a suitable continguous clearance 12 which extends throughout the entire length of said metal tube 7. To form and maintain this clearance 12 between the tubes 1 and 7, the inner wall of the quartz tube 1 is provided, in scattered positions, with a plurality of projections 13 corresponding to the width of the clearance 12 and the metallic tube 7 is held in position within the quartz tube 1 by the forward ends of the projections 13 positioned in pressure contact with the outer wall of the metal tube 7. The provision of such a clearance has the advantage that, when taking a sample of molten metal, the metal is aspirated into the outer side of metal tube as well to assist in alloying and, at the same time, the entry of external hydrogen by a direct contact of the metal tube in which hydrogen is highly soluble with the atmosphere or a cooling medium is prevented.

After the desired specimen of molten metal has been obtained in the described manner, the conventional procedures may be carried out. For example, the sampling device is rapidly cooled to atmospheric temperature, for example with water, and the specimen is allowed to stand till the time of analysis, while stored in liquid nitrogen or dry ice-alcohol. It is, of course, preferable that the quartz tube 1 is crushed in water at the time of water quenching and thin-walled tube 7 containing the specimen (a primary sample) is cooled as exposed. In carrying out an analysis, the specimen and tube 7 is allowed to return to room temperature and a suitable length of the tube 7 is cut out to obtain a secondary sample. In the determination of hydrogen in molten steel, the weight of the thin-walled tube 7 is computed from the length of the secondary sample, the outer diameter, wall thickness, density and other parameters of the tube 7 and this weight value is used as a correction factor. In connection with this procedure, it is, of course, necessary that the amount of hydrogen in the substance of the thin-walled tube 7 be previously determined. Thus, as it has been mentioned hereinbefore, the inherent hydrogen of the thin-walled tube 7 should be held to a minimum and, in consideration of this, it is recommended that the tube be previously subjected to a thorough dehydrogenation treatment.

EXAMPLE 1

Figure 1A:
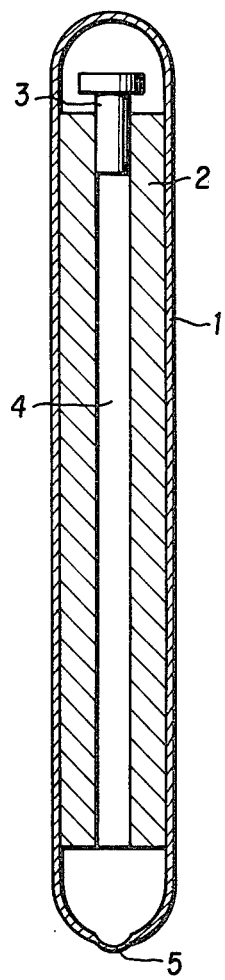
FIG. 1 (A) is a longitudinal cross-sectional view showing a prior art sampling device for taking specimens for determination of hydrogen in a molten metal.
Figure 1B:
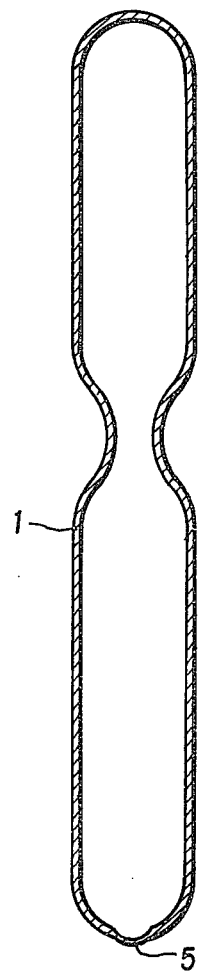

Using the sampling device according to this invention, the amounts of hydrogen in a molten steel bath and a teeming stream of steel, both containing 0.45% of carbon, were determined. The outer and inner diameters of the quartz tube 1 employed were 9 mm and 7 mm, respectively, and the other and inner diameters and the length of the thin-walled austenite steel tube 7 were 6.5 mm, 5.6 mm and 100 mm, respectively. The distance between the forward end of the paper sleeve 6 and the forward end of the quartz tube 1 was 30 mm. For a determination of hydrogen in the teeming stream, the sampling device shown in FIG. 3 was employed. The specifications of the quartz tube of this device were the same as those of the device of FIG. 2. The values of $t_1$ and $t_2$ in FIG. 3 were 15 mm and 20 mm, respectively. The results are set forth in FIG. 6. It will be seen that the use of the sampling device according to this invention consistently produced results higher than the results obtained by the use of the conventional sampling device shown in FIG. 1 (B). It is considered that the values obtained by the present invention better approximate the true values. FIG. 7 is a typical hydrogen segregation diagram of the primary sample, indicating that highly stable results are obtained in a central part of the thin-walled tube.

A typical analysis of the distribution of hydrogen in the thin-walled tube 7 versus the solidified metal shows that the value for the former was 5.18 ppm and the value for the latter was 3.89 ppm. The hydrogen concentration of the molten steel bath as calculated with their weight ratio being taken into consideration was 5.74 ppm. The hydrogen in the same molten steel bath as measured by the prior art method was 3.91 ppm which is in close proximity with the value of 3.89.

It is thus clear that, by measuring the amount of hydrogen lost into the thin-walled tube 7, it is for the first time possible obtain a nearly accurate hydrogen analysis.

EXAMPLE II

Figure 7:
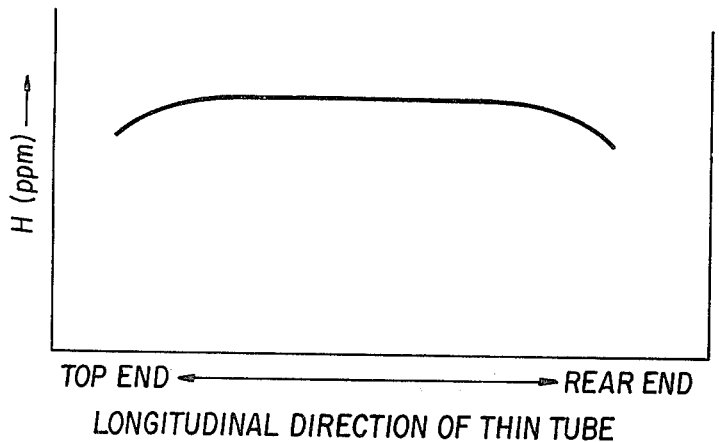
FIG. 7 is a graphic representation showing the relationship between the part of the specimen taken in the sampling device with the hydrogen value obtained.
Figure 8:
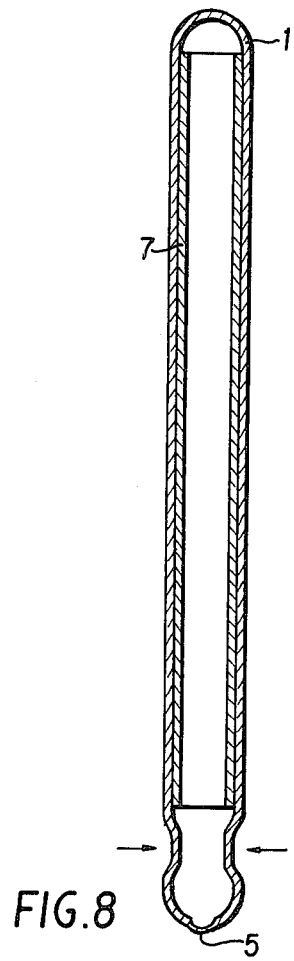
FIG. 8 is a longitudinal cross-sectional view showing a further embodiment of the sampling device according to this invention.

The amounts of hydrogen in a molten steel bath and a teeming stream of molten steel, both containing 0.45% of carbon as in Example 1, were determined. In the determination of hydrogen in the molten steel bath, the sampling device of FIG. 4 was employed. However, the outer and inner diameters of the quartz tube were 11 mmd and 9 mm, respectively the outer and inner diameters and the length of the metallic tube 7 (pure Ti) were 7.5 mm, 6.5 mm and 100 mm, respectively; and the distance between the forward end of the paper sleeve 6 and the forward end of the quartz tube 1 was 30 mm. For an analysis of the teeming stream for hydrogen, the device shown in FIG. 5 was employed. The specifications of the quartz tube of this device were the same as those of the corresponding member of the device of FIG. 4. The values of $t_1$ and $t_2$ were 15 mm and 20 mm, respectively. The results were substantially identical with the data obtained in Example 1 and shown in FIG. 6 and FIG. 7. FIG. 8 shows a sampling device of the invention for use in laboratory scale test in which concave portions indicated by arrows are provided to prevent cracks even if at top end portion of the device, undue pressure has applied thereto.

Having the foregoing construction, this invention has the following advantages.

(1) The hydrogen in molten metal is less easily lost in the course of sampling and solidification so that a more accurate hydrogen analysis can be performed.

(2) The variance of results due to the experience and skill of the analyst is reduced.

(3) Since the thin-walled tube and solidified metal are analyzed together, the method does not require a two-step procedure such as the aforementioned vacuum-mould method, and ensures a higher degree of precision.

Figure 6:
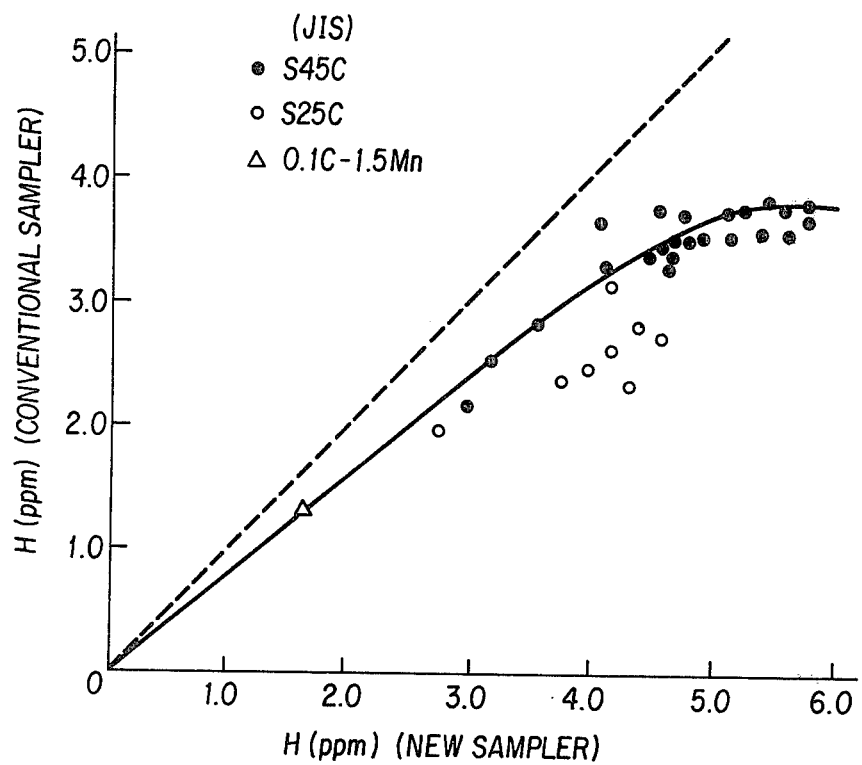
FIG. 6 is a graphic representation showing the performance of the sampling device of this invention as compared with the performance of the prior art sampling device.

(4) As will be seen from FIG. 6, the utility of the sampling device according to this invention is particularly great when the hydrogen level is high. Therefore, this invention is particularly useful in hydrogen determination of liquid steel, where adjustments of hydrogen content are very important.

Obviously, many modifications and variations of the present invention are possible in light of the above teachings. It is therefore to be understood that within the scope of the appended claims, the invention may be practiced otherwise than as specifically described thereon.

What is claimed as new and desired to be secured by letters patent of the United States is:

1. A sampling device for a determination of hydrogen in molten metal which comprises a refractory containment member having a thin-walled portion comparatively prepared to be destroyed by an external force and a material in which hydrogen is relatively non-diffusible or readily soluble, said material being housed in said refractory containment member and either a vacuum or a reduced pressure being maintained with said containment member.

2. A sampling device according to claim 1 wherein a tubular member composed of a metallic material capable of alloying with a molten metal to be sampled is inserted and disposed in said refractory containment member with the provision for a clearance between the outer wall of said tubular member and the inner wall of said refractory containment member.

3. A sampling device according to claim 1 wherein said refractory member comprises quartz and a tubular member of austenite stainless steel is disposed within said refractory containment member with a substantial vacuum being established with said containment member and said thin-walled portion comparatively prepared to be destroyed by an external force being located at a forward end of said refractory containment member.

4. A sampling device according to claim 1 wherein said refractory containment member has a curved portion at a forward end thereof.

5. A sampling device according to claim 2 wherein said refractory containment member has a curved portion at a forward end thereof.

6. A sampling device according to claim 2 wherein said refractory containment member is provided, contiguous with its inner wall, with a plurality of projections extending toward the axis thereof to maintain a clearance between said refractory containment member and said alloying metal member.

7. A sampling device according to claim 6 wherein said alloying metal member comprises a tube of titanium.

* * * * *